(12) United States Patent
Nakagawa

(10) Patent No.: US 8,571,646 B2
(45) Date of Patent: Oct. 29, 2013

(54) EMOTIONAL STATE DETERMINING APPARATUS

(75) Inventor: Masahiro Nakagawa, Nagaoka (JP)

(73) Assignee: National University Corporation Nagaoka University of Technology, Niigata (JP)

( * ) Notice: Subject to any disclaimer, the term of this patent is extended or adjusted under 35 U.S.C. 154(b) by 333 days.

(21) Appl. No.: 13/201,048

(22) PCT Filed: Feb. 12, 2010

(86) PCT No.: PCT/JP2010/052037
§ 371 (c)(1),
(2), (4) Date: Aug. 11, 2011

(87) PCT Pub. No.: WO2010/093007
PCT Pub. Date: Aug. 19, 2010

(65) Prior Publication Data
US 2011/0319784 A1 Dec. 29, 2011

(30) Foreign Application Priority Data
Feb. 12, 2009 (JP) .................... 2009-030391

(51) Int. Cl.
*A61B 5/04* (2006.01)
(52) U.S. Cl.
USPC ........................................... 600/544
(58) Field of Classification Search
USPC ................................ 600/544, 545
See application file for complete search history.

(56) References Cited

U.S. PATENT DOCUMENTS

| 5,601,090 A * | 2/1997 | Musha | 600/544 |
| 2005/0107716 A1* | 5/2005 | Eaton et al. | 600/544 |
| 2005/0277813 A1* | 12/2005 | Katz et al. | 600/300 |
| 2009/0259137 A1* | 10/2009 | Delic et al. | 600/545 |

FOREIGN PATENT DOCUMENTS

JP 2004-194924 7/2004

OTHER PUBLICATIONS

Nakagawa, M.: "Chaos and Fractals in Engineering", published by World Scientific (1999).
International Search Report: Corresponding Published PCT Application No. WO2010093007 (PCT No. PCT/JP2010052037); Japanese Patent Office; Issued May 18, 2010.
Ogo, K. et al.: "On the Chaos and Fractal Properties in EEG Data", IEICE Trans. A Vo. J78-A No. 2, pp. 161-168 (Feb. 1995).

(Continued)

*Primary Examiner* — Navin Natnithithadha
*Assistant Examiner* — Etsub Berhanu
(74) *Attorney, Agent, or Firm* — Benesch Friedlander Coplan & Aronoff, LLP

(57) ABSTRACT

An emotional state determining apparatus capable of determining an emotional state of a subject without reducing determination accuracy even if the number of brain wave signals to be used is reduced. A multifractal dimension computing section 3 computes multifractal dimensions based on brain wave signals or brain wave difference signals. An emotional state determining section 4 receives input data on the multifractal dimensions, and determines an emotional state of the subject based on determination criteria which are determined in advance by using as reference data the brain wave signals obtained from a reference person. Generalized latent dimensions (vector) respectively obtained by substituting a plurality of different values determined in advance for a Hurst exponent characteristic q in a generalized latent dimension $Dq=1/Hq$, which is a reciprocal number of a generalized Hurst exponent Hq obtained from the brain wave signals or the brain wave difference signals, are used as the multifractal dimensions.

8 Claims, 13 Drawing Sheets

(56) References Cited

OTHER PUBLICATIONS

Ogo, K. et al.: "Chaos and Fractal Properties in EEG Data", Electronics and Communications in Japan, Part 3, vol. 78 No. 10 (1995).
Iizuka, T. et al.: "An Application of EEG Analyses Based on Fractal Theory to Emotion Information Processing", Technical Report of IEICE. NLP2004-124 (Mar. 2005).
Sato, T. et al.: "Quantification of Emotions using Fractal Dimension and Analysis—Emotional Fractal-Dimension Analysis Method", Technical Report of IEICE, HIP2002-45 (Dec. 2002).
Matsushita, S. et al.: "Emotional Information Analysis Using Optical Topography", IEICE Trans. A vol. J88-A No. 8, pp. 994-1001 (2005).
Iizuka, T. et al.: "On the Human Interface with Fractal Dimension Analysis of EEG", Technical Report of IEICE, CAS2005-41 NLP2005-54 (Sep. 2005).
Ito, N. et al.; "A Study of Spatio-Temporal Characteristics of EEG Based on the Multifractual Analysis", Technical Report of IEICE. MBE95-70 (Sep. 1995).
Phothisonothai, M. et al.: "EEG-Based Classification of Motor Imagery Tasks Using Fractal Dimension and Network for Brain-Computer Interface", IEICE Trans. Ine & Syst., vol. E91-D, No. 1 (Jan. 2008).

\* cited by examiner

Fig. 9

Difference between Emotion Output and Subjective Evaluation

| Subject | GORGEOUS Impression | SIMPLE Impression |
|---------|---------------------|-------------------|
| A | 0.82 → 0.94 | 0.65 → 0.88 |
| B | 0.97 → 0.99 | 0.38 → 0.54 |
| C | 0.79 → 0.81 | 0.64 → 0.69 |
| D | 0.75 → 0.81 | 0.86 → 0.91 |

US 8,571,646 B2

EMOTIONAL STATE DETERMINING APPARATUS

CROSS REFERENCE TO RELATED APPLICATIONS

This application is a U.S. National Stage of PCT/JP2010/052037 filed Feb. 12, 2010, which claims priority to Japanese Application No. 2009-030391 filed on Feb. 12, 2009. The entirety of this Application is incorporated herein by reference.

TECHNICAL FIELD

The present invention relates to an emotional state determining apparatus that can determine an emotional state of a subject.

BACKGROUND ART

Human emotions are generally considered to be characterized by brain activities. The states of the brain activities can be observed by using brain waves or the like, and various studies are currently made on the states of the brain activities by using the brain waves. Since the measurement of brain wave signals require no muscular motion, the wave signals can be easily measured compared to MEG and fMRI, and reflect the states of the brain activities. Therefore, the brain wave signals are expected to be applied to various fields. Further, it has become known that the brain waves have fractal properties, and studies have been made to elucidate the states of the brain activities by performing a fractal analysis on the brain wave signals as shown in [Non-Patent Document 1: OGO, Kiyotaka and NAKAGAWA, Masahiro, "On the Chaos and Fractal Properties in EEG Data", Transactions of IEICE, Vol. J78-A, No. 2, pp. 161-168 (1995)], [Non-Patent Document 2: OGO, Kiyotaka and NAKAGAWA, Masahiro, "On the Chaos and Fractal Properties in EEG Data", Electronics and Communications in Japan, Part III-Fundamentals, Vol. 78-10, pp. 27-36 (1995)], and [Non-Patent Document 3: NAKAGAWA, Masahiro, "Chaos and Fractals in Engineering", World Scientific, Inc (1999)].

An emotion fractal dimension analysis technique has been proposed as a technique for quantitatively evaluating an emotion ("angry", "sad", "happy", and "relaxed") by characteristically using fractal dimensions obtained by separating a plurality of brain wave signals measured from a subject into a plurality of bands determined in advance, preparing a mutual correlation signal for the plurality of band-separated brain wave signals by calculating a difference between or a product of two brain wave signals selected from the plurality of band-separated brain wave signals, and performing a fractal dimension analysis on the mutual correlation signal as shown in [Non-Patent Document 4: SATO, Takahiro and NAKAGAWA, Masahiro, "Quantification of Emotions Using Fractal Dimension Analysis", Technical Report of IEICE, HIP2002-12, pp. 13-18, 2002] and [Patent Document 1: Japanese Patent Application Publication No. 2004-194924]. Other technologies that utilize the emotion fractal dimension analysis technique include a technology for analyzing emotional information using optical topography as shown in [Non-Patent Document 5: MATSUSHITA, Shin and NAKAGAWA, Masahiro, "Emotional Information Analysis using Optical Topography", Transactions of IEICE, Vol. J88-A, No. 8, pp. 994-1001] and a technology for application to human interfaces as shown in [Non-Patent Document 6: IIZUKA, Takuya and NAKAGAWA, Masahiro "Application to Human Interfaces Using Fractal Dimension Analysis on Brain Waves", Technical Report of IEICE, CAS2005-42, NLP2005-54 (2005)].

Further, an emotion fractal dimension analysis technique that uses the fractal properties of brain waves as a characteristic amount has been proposed as a technique for quantitatively evaluating human emotions as shown in [Non-Patent Document 7: ITO, Naoko, KOMORI, Koki, and NAKAGAWA, Masahiro, "A Study of Spatio-Temporal Characteristics of EEG Based on the Multifractal Analysis", Technical Report of IEICE, MBE95-70, 1995].

[Patent Document 1] Japanese Patent Application Publication No. 2004-194924

[Non-Patent Document 1] "On the Chaos and Fractal Properties in EEG Data", Transactions of IEICE, Vol. J78-A, No. 2, pp. 161-168 (1995)

[Non-Patent Document 2] "On the Chaos and Fractal Properties in EEG Data", Electronics and Communications in Japan, Part III-Fundamentals, Vol. 78-10, pp. 27-36 (1995)

[Non-Patent Document 3] "Chaos and Fractals in Engineering", World Scientific, Inc (1999)

[Non-Patent Document 4] "Quantification of Emotions using Fractal Dimension Analysis", Technical Report of IEICE, HIP2002-12, pp. 13-18, 2002

[Non-Patent Document 5] "Emotional Information Analysis using Optical Topography", Transactions of IEICE, Vol. J88-A, No. 8, pp. 994-1001

[Non-Patent Document 6] "Application to Human Interfaces Using Fractal Dimension Analysis on Brain Waves", Technical Report of IEICE, CAS2005-42, NLP2005-54 (2005)

[Non-Patent Document 7] ITO, Naoko, KOMORI, Koki, and NAKAGAWA, Masahiro, "A Study of Spatio-Temporal Characteristics of EEG Based on the Multifractal Analysis", Technical Report of IEICE, MBE95-70, 1995

DISCLOSURE OF INVENTION

Technical Problem

With the conventional techniques which use multifractal dimensions, it is difficult to reduce the number of brain wave signals to be measured without reducing the accuracy.

An object of the present invention is to provide an emotional state determining apparatus that can determine an emotional state of a subject without reducing the determination accuracy even if the number of brain wave signals to be used is reduced.

Solution to Problem

An emotional state determining apparatus according to the present invention includes a multifractal dimension computing section and an emotional state determining section. The multifractal dimension computing section computes multifractal dimensions based on one or more brain wave signals measured from one or more regions of a subject's brain, or based on one or more brain wave difference signals which are obtained as a difference between two different brain wave signals in one or more sets of the two different brain wave signals that are selected from a plurality of brain wave signals measured from a plurality of regions of the subject's brain. If the brain wave difference signals are used, the emotional state determining apparatus may further include a brain wave difference signal computing section. The brain wave difference signal computing section computes difference signals for a plurality of sets of two different brain wave signals. The plurality of sets of brain wave signals are selected in terms of permutations from the plurality of brain wave signals measured from the plurality of regions of the subject's brain to output resulting difference signals as the one or more brain wave difference signals. If the brain wave difference signals are not used, the brain wave signals are input, as they are, to the multifractal dimension computing section. Specifically, the difference signals are computed in each short time period, and the multifractal dimension computing section performs an emotion fractal dimension analysis on the difference signals computed in each short time period to compute the multifractal dimensions in each short time period.

In the present invention, the emotional state determining section receives input data on the multifractal dimensions, and determines an emotional state of the subject based on determination criteria which are determined in advance by using as reference data the one or more brain wave signals or the one or more brain wave difference signals obtained from a reference person in each of a plurality of types of emotional states determined in advance. The reference person can be in the plurality of types of emotional states (a variety of states defined by emotions that can be felt by a human being, such as feeling rested, happy, or sad, and having a gorgeous impression or a simple impression). The reference person is preferably a person who has common sensibilities, and may be the subject himself/herself.

The emotional state determining section includes a storage section that stores the determination criteria, and a determining section that determines in what state, being at rest or being in other emotional states of a plurality of types, the subject is, based on the determination criteria and the data on the multifractal dimensions. The determination criteria stored in the storage section are defined as follows. First, reference multifractal dimensions are computed based on the one or more brain wave signals or the one or more brain wave difference signals obtained as the reference data from the reference person in each of the plurality of types of emotional states. Then, the determination criteria are defined such that, when the reference multifractal dimensions for each of the plurality of types of emotional states are input to the determining section, the determining section correctly determines the emotional state corresponding to the input reference multifractal dimensions.

In the present invention, the multifractal dimensions are generalized latent dimensions $Dq_1$ to $Dq_n$ respectively obtained by substituting n different values ($q_1$ to $q_n$) determined in advance for a Hurst exponent characteristic q in a generalized latent dimension $Dq=1/Hq$ which is a reciprocal number of a generalized Hurst exponent Hq obtained from the one or more brain wave signals or the one or more brain wave difference signals, where $q_1$ to $q_n$ are each a positive number and n is a positive integer of 2 or more.

The generalized Hurst exponent Hq is represented by the following formula:

$$H_q = \frac{1}{q} \frac{\partial \log \sigma_q(\tau)}{\partial \log \tau} \quad \text{[Expression 1]}$$

where $\tau$ is the sampling period of the time-series data, and $\sigma_q(\tau)$ is the generalized moment for the time series F(t).

The present invention is based on a finding that the generalized latent dimensions $Dq_1$ to $Dq_n$ are effective in determining an emotional state. The generalized Hurst exponent Hq has been used to estimate affine fractal dimensions with q in the above formula set to q=2 (fixed). When the inventor computed a plurality of generalized latent dimensions $Dq_1$ to $Dq_n$ by substituting a plurality of different values ($q_1$ to $q_n$) for q in the generalized Hurst exponent Hq, it was found that the dispersion of the plurality of generalized latent dimensions $Dq_1$ to $Dq_n$ with respect to the value of q differed among various types of emotional states.

When an emotion analysis was performed using the generalized latent dimensions $Dq_1$ to $Dq_n$ as the multifractal dimensions based on the foregoing finding, it was confirmed that the emotion analysis was effectively performed. By using the generalized latent dimensions $Dq_1$ to $Dq_n$ as the multifractal dimensions, a desired number of multifractal dimensions can be obtained by increasing the number of values of q in the above formula.

For example, an emotion analysis may be performed using five generalized latent dimensions $Dq_1$ to $Dq_5$ computed by adopting five values as the value of q even if only one brain wave signal or brain wave difference signal is detected. In such a case, it is possible to obtain emotion information which is similar to that obtained when an emotion analysis is performed using five brain wave signals or brain wave difference signals.

As a result, according to the present invention, it is possible to effectively perform an emotion analysis by increasing the number of values of q without reducing the accuracy even if the number of brain wave signals to be used is small (one brain waveform is used).

The determining section may be configured to determine m types of emotional states according to a linear mapping determination technique using the following determination formula:

$$\begin{pmatrix} C_{1,1} & C_{1,2} & \cdots & \cdots & C_{1,x} \\ \vdots & \vdots & \ddots & & C_{2,x} \\ \vdots & \vdots & & \ddots & \vdots \\ C_{m,1} & C_{m,2} & \cdots & \cdots & C_{m,x} \end{pmatrix} \begin{pmatrix} y_1 \\ \vdots \\ y_x \end{pmatrix} + \begin{pmatrix} d_1 \\ d_2 \\ \vdots \\ d_m \end{pmatrix} = \begin{pmatrix} z_1 \\ z_2 \\ \vdots \\ z_m \end{pmatrix} \quad \text{[Expression 2]}$$

where m is a positive integer of 2 or more, and x is a number represented by x=p×n with the proviso that p is the number of the one or more brain wave signals or the one or more brain wave difference signals.

In the above formula:

$$\begin{pmatrix} C_{1,1} & C_{1,2} & \cdots & \cdots & C_{1,x} \\ \vdots & \vdots & \ddots & & C_{2,x} \\ \vdots & \vdots & & \ddots & \vdots \\ C_{m,1} & C_{m,2} & \cdots & \cdots & C_{m,x} \end{pmatrix} \quad \text{[Expression 3]}$$

The above expression is a state separating matrix which is a linear mapping;

$$\begin{pmatrix} y_1 \\ \vdots \\ y_x \end{pmatrix} \quad \text{[Expression 4]}$$

This above expression is an input signal vector;

$$\begin{pmatrix} d_1 \\ d_2 \\ \vdots \\ d_m \end{pmatrix} \quad \text{[Expression 5]}$$

The above expression is a constant vector; and $$\begin{pmatrix} z_1 \\ z_2 \\ \vdots \\ z_m \end{pmatrix} \quad \text{[Expression 6]}$$

The above expression is a computation result indicating an emotional state which should be determined as one of the m types of emotional states.

The state separating matrix discussed above is used as the determination criteria. If the brain wave difference signals are used, the emotional state determining apparatus may further include a state separating matrix determining section to obtain such a state separating matrix. The brain wave difference signal computing section computes the one or more brain wave difference signals which are obtained as a difference between two different brain wave signals in one or more sets of the two different brain wave signals that are selected from two or more brain wave signals measured from two or more regions of the subject's brain in each of the plurality of types of emotional states. Then, the multifractal dimension computing section computes the multifractal dimensions based on the one or more brain wave difference signals. The state separating matrix determining section receives the multifractal dimensions as the input signal vector for the determination formula, and determines the state separating matrix and the constant vector in advance such that, when the reference person is in each of the plurality of types (m types) of emotional states, the computation result of the determination formula indicates an emotional state corresponding to one of the m types of emotional states.

The emotional state determining section may be configured to determine an emotional state using a neural net as the determination criteria. If the plurality of brain wave difference signals are used, an internal state of the neural net is determined as follows. The plurality of brain wave difference signals are first computed from the plurality of brain wave signals obtained from the reference person in each of the plurality of types (m types) of emotional states; the multifractal dimensions are computed based on the plurality of brain wave difference signals; the multifractal dimensions for the plurality of types (m types) of emotional states are defined as a plurality of types (m types) of learning input patterns; and learning is performed using sequentially input data on the learning input patterns selected regularly at predetermined time intervals or irregularly from the plurality of types (m types) of learning input patterns.

By using such a neural net as the determination criteria, the determination accuracy can be enhanced compared to when a state separating matrix, which is a linear mapping, is used as the determination criteria. The internal state of the neural net can be improved to a level required to perform a determination with high accuracy in a short learning time particularly when the internal state of the neural net is determined through learning, by defining the multifractal dimensions for the plurality of types of emotional states as a plurality of types of learning input patterns, and learning using sequentially input data on the learning input patterns selected regularly at predetermined time intervals or irregularly from the plurality of types of learning input patterns.

The state matrix determining section may be used when one or more brain wave signals are measured with one electrode for measurement disposed at a head portion of the subject so that the one or more brain wave signals are used as they are. However, noise may inevitably be influential when brain wave signals are used as they are, rather than when brain wave difference signals are used. Even if the brain wave signals are directly used, information required to perform an emotion analysis can be obtained by increasing the number of values of q in the generalized Hurst exponent Hq described above compared to when the brain wave difference signals are used, thereby causing no practical problem.

BRIEF DESCRIPTION OF DRAWINGS

FIG. 9 compares a conventional technique and the embodiment of the present invention in respect of correlation coefficient.

BEST MODE FOR CARRYING OUT THE INVENTION

Figure 1:
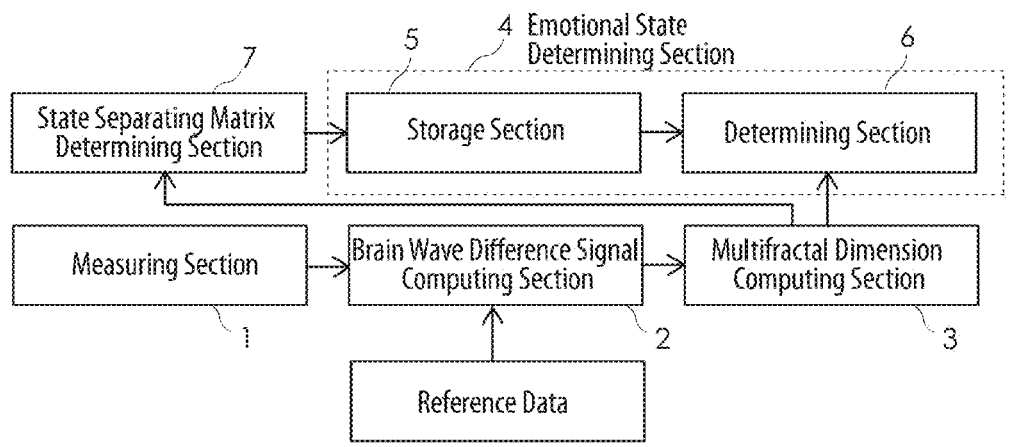
FIG. 1 is a block diagram schematically showing an example configuration of an emotional state determining apparatus according to an embodiment of the present invention.

Now, embodiments of the present invention will be described in detail below with reference to the drawings. FIG. 1 is a block diagram schematically showing an example configuration of an emotional state determining apparatus according to an embodiment of the present invention. In the embodiment, in order to generalize the present invention, brain wave signals for 16 channels measured from 16 regions of a brain including a temporal lobe portion are used. In practice, as described later, the present invention may also be applicable when using only a brain wave signal for one channel is used and when a brain wave difference signal which is obtained as a difference between brain wave signals for two channels.

In the embodiment, a plurality of types of emotional states of a human being (subject) are quantitatively evaluated through signal processing and a determination process that use an emotion multifractal dimension analysis technique. An emotional state determining apparatus shown in FIG. 1 includes a measuring section 1, a brain wave difference signal computing section 2, a multifractal dimension computing section 3, and an emotional state determining section 4 as constituent sections forming a basic configuration of the embodiment in which one or more brain wave difference signals are used. The emotional state determining section 4 includes a storage section 5 and a determining section 6. In the embodiment, the emotional state determining apparatus further includes a state separating matrix determining section 7 that determines a state separating matrix to be used as determination criteria which will be described later.

Figure 2:
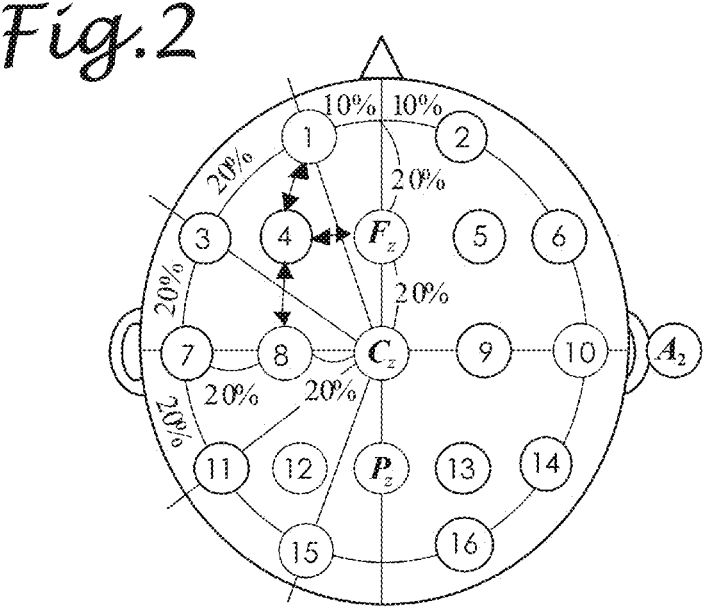
FIG. 2 illustrates an arrangement of electrodes for 16 channels.

The measuring section 1 is formed by a known electroencephalograph that measures brain wave signals for 16 channels with electrodes disposed in 16 regions of a brain as shown in FIG. 2. Thus, the measuring section 1 outputs brain wave signals for 16 channels to the brain wave difference signal computing section 2.

Figure 3:
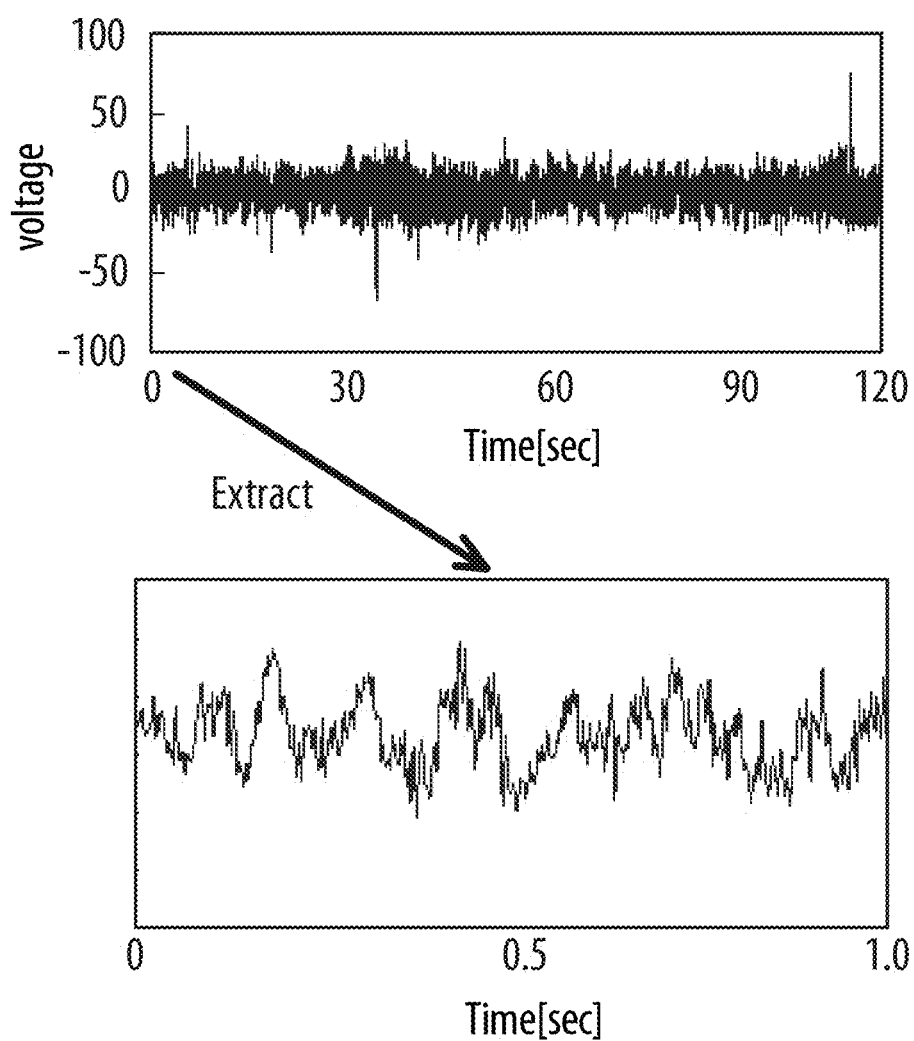
FIG. 3 illustrates how a signal is extracted.

The brain wave difference signal computing section 2 is configured to compute difference signals for a plurality of sets of two different brain wave signals (120 sets of difference signals). The plurality of sets of brain wave signals are selected in terms of permutations from the brain wave signals for 16 channels to output the resulting difference signals as 120 sets of brain wave difference signals. The brain wave difference signal computing section 2 computes the brain wave difference signals in each short time period. FIG. 3 illustrates how a portion of a brain wave difference signal is extracted from the brain wave difference signal in each short time period.

The multifractal dimension computing section 3 is configured to compute multifractal dimensions based on signals extracted from the 120 sets of brain wave difference signals output from the brain wave difference signal computing section 2. Computation of the multifractal dimensions will be described later. The multifractal dimension computing section 3 also performs an emotion fractal dimension analysis on the difference signals computed in each short time period to compute the fractal dimensions in each short time period.

The emotional state determining section 4 measures brain waves to be used as learning data in advance to perform time-dependent multifractal dimension estimation. In a specific example, learning and recognition are performed using a linear mapping as an input signal such that independent outputs are provided in connection with respective emotions to quantitatively identify an emotion with the data on brain waves to be evaluated.

To this end, the storage section 5 stores as a state separating matrix determination criteria determined in advance using as reference data a plurality of brain wave signals obtained from a reference person in each of a plurality of types of emotional states. The reference person can intentionally enter into each of a state of being at rest and the plurality of types of emotional states. Then, the determining section 6 determines one of the state of being at rest and the plurality of types of emotional states as the emotional state of the subject based on input data on the multifractal dimensions computed by the multifractal dimension computing section 3. The determination criteria stored in the storage section 5 have been determined by the state separating matrix determining section 7. The state separating matrix determining section 7 determines the state separating matrix such that, when the multifractal dimensions for each of the plurality of types of emotional states are input to the determining section 6, the determining section 6 correctly determines the emotional state corresponding to the input multifractal dimensions, wherein the brain wave difference signal computing section 2 computes the plurality of brain wave difference signals from the plurality of brain wave signals (reference data) obtained from the reference person in each of the plurality of types of emotional states, and the multifractal dimension computing section 3 computes the multifractal dimensions based on the plurality of brain wave difference signals. The state separating matrix determining section 7 then causes the storage section 5 to store the determined state separating matrix.

Determination performed by the emotional state determining section 4 according to the embodiment, along with computation performed by the multifractal dimension computing section 3, will be described in further detail. A multifractal dimension estimation method based on the scaling properties of dispersion is known as a method of estimating multifractal dimensions of brain wave signals. A q-th order generalized moment $\sigma_q$ ($0<q<+\infty$) of data $f(t+\tau)$, which are distant by time $\tau$ from time-series data $f(t)$ with multifractal dimensions Dq, is represented by the following formula:

$$\sigma_q(\tau) = \langle |f(t+\tau) - f(t)|^q \rangle \quad \text{[Expression 7]}$$

Figure 4:
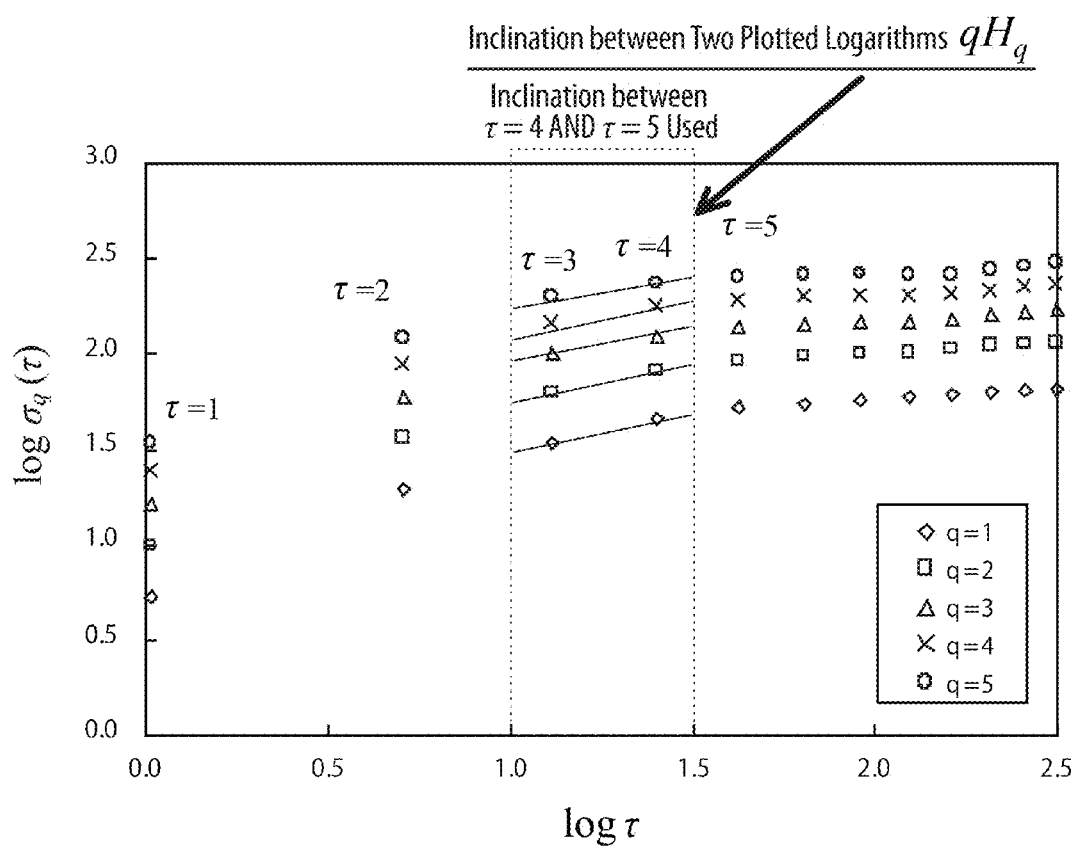
FIG. 4 illustrates scaling properties of a generalized Hurst exponent.

In FIG. 4, the vertical axis and the horizontal axis on the paper of the figure indicate the logarithm log $\sigma_q(\tau)$ and the logarithm log $\tau$, respectively, of the generalized moment $\sigma_q$. As shown in FIG. 4, a generalized Hurst exponent is computed based on the inclination [qHq] of the scaling properties of the time-series data with $\tau$ varied as follows. In the embodiment, $\tau$ is a value of 4 to 5.

$$H_q = \frac{1}{q} \frac{\partial \log \sigma_q(\tau)}{\partial \log \tau} \quad \text{[Expression 8]}$$

In the present invention, a plurality of generalized latent dimensions $Dq_1$ to $Dq_n$ obtained by substituting a plurality of different values $q_1$ to $q_n$ determined in advance for a Hurst exponent characteristic (order) q in a generalized latent dimension Dq=1/Hq which is a reciprocal number of a generalized Hurst exponent Hq are used as the multifractal dimensions, where $q_1$ to $q_n$ are each a positive number and n is a positive integer.

The following experiment confirmed that the generalized latent dimensions $Dq_1$ to $Dq_n$ could be used as the multifractal dimensions. That is, in the experiment, the generalized Hurst exponent Hq for a difference signal (brain wave difference signal) between two signals from two electrodes attached to a front side of a head portion of the subject was varied in five steps with the Hurst exponent characteristic q varied from $q_1=1$ to $q_5=5$ with the subject in a state of being at rest, a "state of looking at a gorgeous photograph", and a "state of looking at a simple photograph". In the experiment, only one brain wave difference signal was used. The experiment confirmed that the effect of the present invention was obtained even if only one brain wave difference signal was used.

Figure 5:
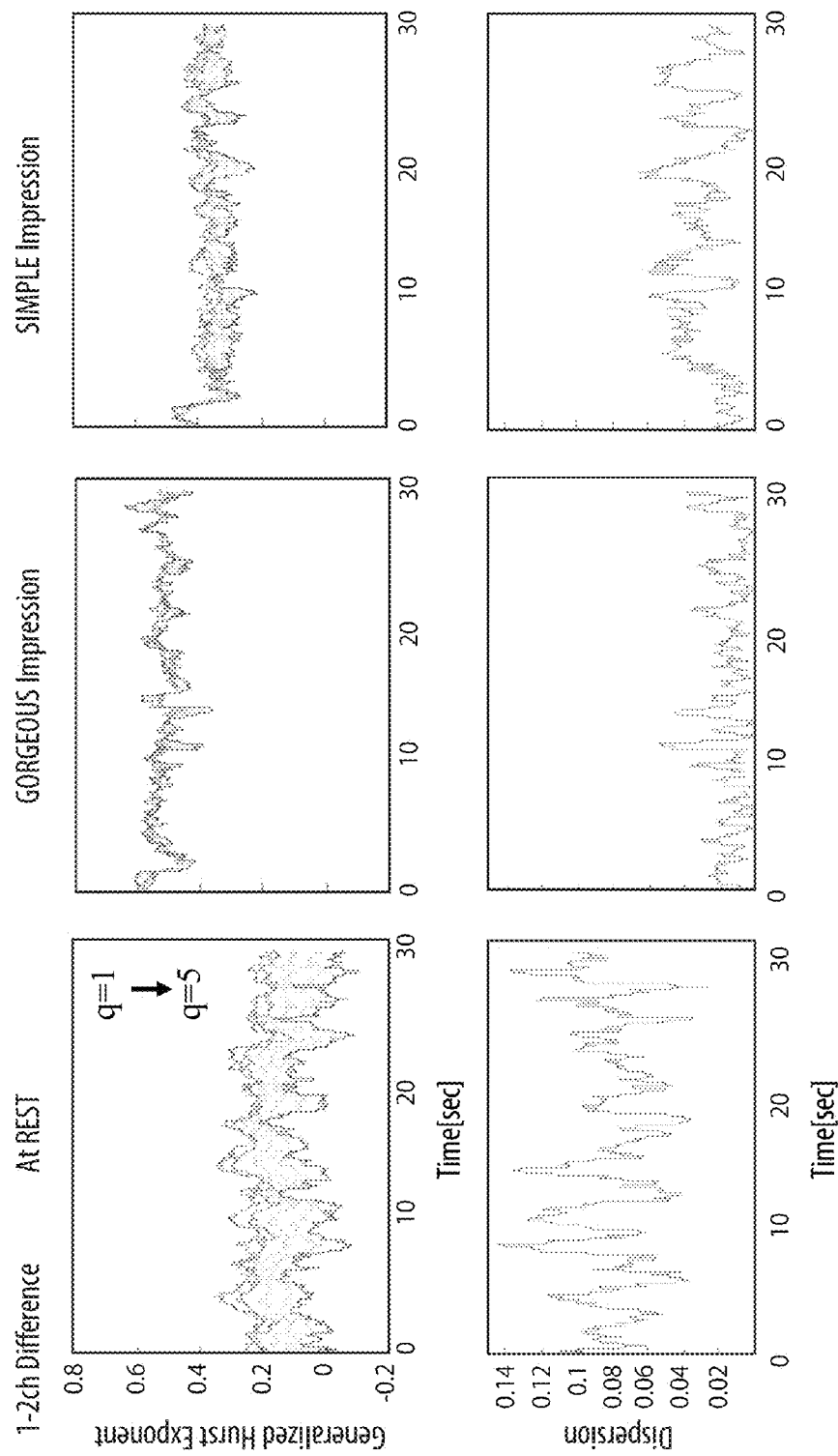
FIG. 5 illustrates an example result of analyzing the generalized Hurst exponent for a brain wave difference signal for 1-2 channels.

FIG. 5 illustrates temporal changes of generalized Hurst exponent Hq when the Hurst exponent characteristic (order) q varies from $q_1$ to $q_5$, that is, 1, 2, 3, 4, and 5, in respect of the three emotional states which the subject is in, namely, being at rest, having a gorgeous impression, and having a simple impression. It is found from FIG. 5 that the dispersion pattern of the generalized Hurst exponent Hq with respect to variations in q differs among the three emotional states (being at rest, having a gorgeous impression, and having a simple impression). As found from FIG. 5, it is effective to perform an emotional analysis based on the multifractal dimensions which utilize the generalized Hurst exponent Hq since the dispersion pattern of the generalized Hurst exponent Hq with respect to q differs among the three emotional states. The present invention has been made based on such findings. A generalized latent dimension Dq=1/Hq, which is a reciprocal number of the generalized Hurst exponent Hq, exhibits the multifractal properties of the complexity of brain waves more clearly than the generalized Hurst exponent Hq itself. Therefore, in the present invention, the generalized latent dimension Dq=1/Hq, which is a reciprocal number of the generalized Hurst exponent Hq, is used as the multifractal dimensions. The present invention may also be implemented by using the generalized Hurst exponent Hq in place of Dq. Specifically, in the present invention, the generalized latent dimension Dq=1/Hq, which is a reciprocal number of the generalized Hurst exponent Hq, is sequentially obtained from the brain wave signals or the brain wave difference signals. Then, the Hurst exponent characteristic q in the generalized latent dimension Dq=1/Hq is substituted by n different values ($q_1$ to $q_n$) determined in advance for the Hurst exponent characteristic q, where $q_1$ to $q_n$ are each a positive number and n is a positive integer of 2 or more. The generalized latent dimensions $Dq_1$ to $Dq_n$ thus obtained are used as the multifractal dimensions. The amount of information is increased as the value of n (the number of values of the Hurst exponent characteristic q) becomes larger. Therefore, it is preferable to appropriately increase the number (n) of values of the Hurst exponent characteristic q particularly when one brain wave signal or one brain wave difference signal is used.

In the embodiment in which the generalized latent dimensions $Dq_1$ to $Dq_n$ are used as the multifractal dimensions, the determining section 6 is configured to determine m types of emotional states according to a linear mapping determination technique using the following determination formula:

$$\begin{pmatrix} C_{1,1} & C_{1,2} & \cdots & \cdots & C_{1,x} \\ \vdots & \vdots & \ddots & & C_{2,x} \\ \vdots & \vdots & & \ddots & \vdots \\ C_{m,1} & C_{m,2} & \cdots & \cdots & C_{m,x} \end{pmatrix} \begin{pmatrix} y_1 \\ \vdots \\ y_x \end{pmatrix} + \begin{pmatrix} d_1 \\ d_2 \\ \vdots \\ d_m \end{pmatrix} = \begin{pmatrix} z_1 \\ z_2 \\ \vdots \\ z_m \end{pmatrix} \quad \text{[Expression 9]}$$

where m is a positive integer of 2 or more, and x is a number represented by x=p×n with the proviso that p is the number of the one or more brain wave signals or the one or more brain wave difference signals.

In the above formula:

$$\begin{pmatrix} C_{1,1} & C_{1,2} & \cdots & \cdots & C_{1,x} \\ \vdots & \vdots & \ddots & & C_{2,x} \\ \vdots & \vdots & & \ddots & \vdots \\ C_{m,1} & C_{m,2} & \cdots & \cdots & C_{m,x} \end{pmatrix} \quad \text{[Expression 10]}$$

The above expression is a state separating matrix which is a linear mapping;

$$\begin{pmatrix} y_1 \\ \vdots \\ y_x \end{pmatrix} \quad \text{[Expression 11]}$$

The above expression is an input signal vector (generalized latent dimension);

$$\begin{pmatrix} d_1 \\ d_2 \\ \vdots \\ d_m \end{pmatrix} \quad \text{[Expression 12]}$$

The above expression is a constant vector; and $$\begin{pmatrix} z_1 \\ z_2 \\ \vdots \\ z_m \end{pmatrix} \quad \text{[Expression 13]}$$

The above expression is a computation result indicating an emotional state for determining the emotional state thus computed as one of the m types of emotional states.

That is, $[C_{1,1}, \ldots, C_{m,x}]$ in the above formula is a linear mapping of the multifractal dimensions (state separating matrix) obtained based on the brain wave difference signals (reference data) of the reference person. The state separating matrix corresponds to the determination criteria stored in the storage section 5.

The state separating matrix is determined by the state matrix determining section 7.

In order to obtain the state separating matrix discussed above when brain wave signals for 16 channels are used, brain wave signals for 16 channels (reference data) are first obtained from a plurality of regions of a person's brain (reference person) who can be intentionally in one of the state of being at rest and the plurality of types of emotional states to provide the determination criteria. As a result of this process, 120 ($=_{16}C_2$) sets of difference signals are prepared. Defining the time in units of sampling period as t, the value input from the i-th electrode as $x_i(t)$, and the value input from the j-th electrode as $x_j(t)$, the difference signal $y_{ij}(t)$ between the electrodes is give by the following formula:

$$y_{ij}(t) = x_i(t) - x_j(t) \quad \text{[Expression 14]}$$

The 120 potential difference signals $y_{ij}(t)$ between the electrodes obtained for data of 16 channels are temporally extracted using a rectangular window with a window width of $t_w=4$ [sec] to obtain a difference signal for the point $t_w$. Defining the movement width of the window as $t_{step}$ and the position of the window as n, the extracted signal $y_{ij}^n$ is represented using a vector by the following formula:

$$y_{ij}^n = \{y_{ij}(t_{step}^n), \ldots, y_{ij}(t_{step}^n + t_w - 1)\} \quad \text{[Expression 15]}$$

The movement width $t_{step}$ of the window is 0.25 [sec]. Based on the scaling properties of the dispersion, a multifractal dimension analysis is performed on each of the extracted difference signals represented by the following formula:

$$y_{ij}^n \quad \text{[Expression 16]}$$

The multifractal dimension computing section 3 computes, as the multifractal dimensions, the generalized latent dimensions $Dq_1$ to $Dq_n$ respectively obtained by substituting n different values ($q_1$ to $q_n$) determined in advance for the Hurst exponent characteristic q in the generalized latent dimension $Dq=1/Hq$ which is a reciprocal number of the generalized Hurst exponent Hq obtained from the plurality of brain wave difference signals, where $q_1$ to $q_n$ are each a positive number and n is a positive integer of 2 or more.

Next, the multifractal dimensions are received as the input signal vector for the determination formula, and the state separating matrix $[C_{1,1}, \ldots, C_{m,x}]$ and the constant vector $[d_1$ to $d_m]$ are determined in advance such that, when the reference person is in each of the m types of emotional states, for example, the computation result $[Z_1, Z_2, \ldots, Z_m]$ of the determination formula indicates an emotional state corresponding to each of the m types of emotional states.

Specifically, it is assumed to determine an emotional state when the subject looks at a photograph, for example. In addition, it is assumed to determine, as the m types of emotional states, three types of emotional states, namely a state in which the subject is at rest, an emotional state in which the subject has a gorgeous impression, an emotional state in which the subject has a simple impression. In this case, the state separating matrix determining section 7 may determine the state separating matrix such that $[Z_1, Z_2, Z_3]=[+1, -1, -1]$ is output in the state in which the subject is at rest, $[Z_1, Z_2, Z_3]=[-1, +1, -1]$ is output in the emotional state in which the subject has a gorgeous impression, and $[Z_1, Z_2, Z_3]=[-1, -1, +1]$ is output in the emotional state in which the subject has a simple impression.

The input signal vector "$y_1, \ldots, y_x$" is formed by the generalized latent dimensions $Dq_1$ to $D1_n$ discussed above for the 120 brain wave difference signals. For example, when the 120 brain wave difference signals obtained from the brain wave signals for 16 channels are used and five different values $q_1$ to $q_5$ are used as the Hurst exponent characteristic q, $x=120\times5=600$, and the input signal vector "$y_1, \ldots, y_{600}$" is represented by the following formula:

$$y_1 \text{ to } y_5 = D_1^{1-2}, D_2^{1-2}, D_3^{1-2}, D_4^{1-2}, D_5^{1-2}$$
$$y_6 \text{ to } y_{10} = D_1^{2-3}, D_2^{2-3}, D_3^{2-3}, D_4^{2-3}, D_5^{2-3}$$
$$\ldots$$
$$\ldots$$
$$y_{596} \text{ to } y_{600} = D_1^{15-16}, D_2^{15-16}, D_3^{15-16}, D_4^{15-16}, D_5^{15-16}$$

where "$D_1^{1-2}$" represents a generalized latent dimension for a brain wave difference signal between a brain wave signal for channel 1 and a brain wave signal for channel 2 in which $q_1$ is used as the Hurst exponent characteristic q; and "$D_5^{15-16}$" represents a generalized latent dimension for a brain wave difference signal between a brain wave signal for channel 15 and a brain wave signal for channel 16 in which $q_5$ is used as the Hurst exponent characteristic q.

According to the related art, since only q=2 is used for 16 channels, thereby resulting in $x=120\times1=120$. Thus, 120 input signal vectors "$y_1, \ldots, y_{120}$" are used. According to the present invention in which five different values $q_1$ to $q_5$ are used as the Hurst exponent characteristic q, information of five times the amount obtained according to the related art can be obtained when the same number of channels are used.

Then, if only one brain wave difference signal which is a difference between brain wave signals for two channels is used and five different values $q_1$ to $q_5$, for example, are used as the Hurst exponent characteristic q, $x=1\times5=5$, and the generalized latent dimensions $Dq_1$ to $Dq_n$ "$y_1, \ldots, y_5$" to be used as the input signal vector are represented by the following formula:

$$y_1 \text{ to } y_5 = D_1^{1-2}, D_2^{1-2}, D_3^{1-2}, D_4^{1-2}, D_5^{1-2}$$

Thus, according to the present invention, even if one brain wave difference signal is used, n generalized latent dimensions $Dq_1$ to $Dq_n$ can be obtained by increasing the number n of values of the Hurst exponent characteristic q. When one brain wave difference signal is used, $C_{1,1}$ to $C_{m,5}$ is used as the state separating matrix.

As described later, if n different values $q_1$ to $q_n$, for example, are used as the Hurst exponent characteristic q when only one brain wave signal for one channel is used, $x=1\times n=n$, and the generalized latent dimensions $Dq_1$ to $Dq_n$ "$y_1, \ldots, y_n$" to be used as the input signal vector are represented by the following formula:

$$y_1 \text{ to } y_n = D_1, D_2, D_3, \ldots, D_{n-1}, D_n$$

Thus, according to the present invention, even if one brain wave signal is used, n generalized latent dimensions $Dq_1$ to $Dq_n$ can be obtained by increasing the number n of values of the Hurst exponent characteristic q. When one brain wave signal is used, $C_{1,1}$ to $C_{m,n}$ is used as the state separating matrix.

Next, the result of a test conducted will be described. The test was intended to confirm if it is possible to quantitatively determine a state in which the subject is at rest, an emotional state in which the subject has a gorgeous impression, and an emotional state in which the subject has a simple impression when brain wave signals for two channels are used, as when brain wave signals for 16 channels are used.

[Test Description]

First, learning data were measured. In learning, brain waves measured with the subject closely observing an image on which the subject had a gorgeous impression and an image on which the subject had a simple impression were used. From a total of four images of "Japanese-style room", "Kinkakuji Temple (gold temple)", "Ginkakuji Temple (silver temple)", and "cherry blossoms", the subject (age 22, female) chose the image of "Kinkakuji Temple" as a gorgeous image and the image of "Japanese-style room" as a simple image. Thereafter, brain waves were measured with the subject who was alternately brought into the state of being at rest and the state of closely observing the images (four images). The brain waves thus measured were used as data to be evaluated, and an emotion analysis was performed for three emotional states of "being at rest", "having a gorgeous impression", and "having a simple impression". Along with the measurement, a subjective evaluation was also performed through a questionnaire survey.

[Measurement Conditions]

MEG-6116M manufactured by Nihon Kohden Corporation was used as an electroencephalograph device. Measured data were recorded on a personal computer through an A/D conversion board (PCM-DAS16S/16 manufactured by Computer Boards Corporation with an A/D conversion resolution of 16 bits and 16 channels). During the measurement, a sampling frequency of 512 Hz was used, and a low-cut filter for 1.5 Hz and a high-cut filter of 100 Hz were set. During the measurement of brain waves, a hum filter for commercial power was used. Measurement sites were determined based on the International 10-20 Electrode Placement System. A single electrode was used for each of channels 1 to 16 with a reference electrode disposed at the right earlobe A2 as shown in FIG. 2. The measurement was performed in a normal environment.

[Measurement]

In acquiring the learning data, the subject was caused to "be at rest", "look at a gorgeous image", and "look at a simple image" for 30 seconds each.

In acquiring the data to be evaluated (under tasks), the subject was caused to "be at rest" for 30 seconds, pause for 5 seconds, look at the photograph of "Japanese-style room" (a simple impression) for 30 seconds, pause for 5 seconds, "be at rest" for 30 seconds, pause for 5 seconds, look at the photograph of "Kinkakuji Temple" (a gorgeous impression) for 30 seconds, pause for 5 seconds, "be rest" for 30 seconds, pause for 5 seconds, look at the photograph of "Ginkakuji Temple" (a simple impression) for 30 seconds, pause for 5 seconds, "be rest" for 30 seconds, pause for 5 seconds, and look at the photograph of "cherry blossoms" (a gorgeous impression) for 30 seconds. In the subjective questionnaire survey, the subject made evaluations in seven steps between "simple" and "gorgeous".

[Analysis Results]

Emotion Multifractal Dimension Analysis Results

Figure 6:
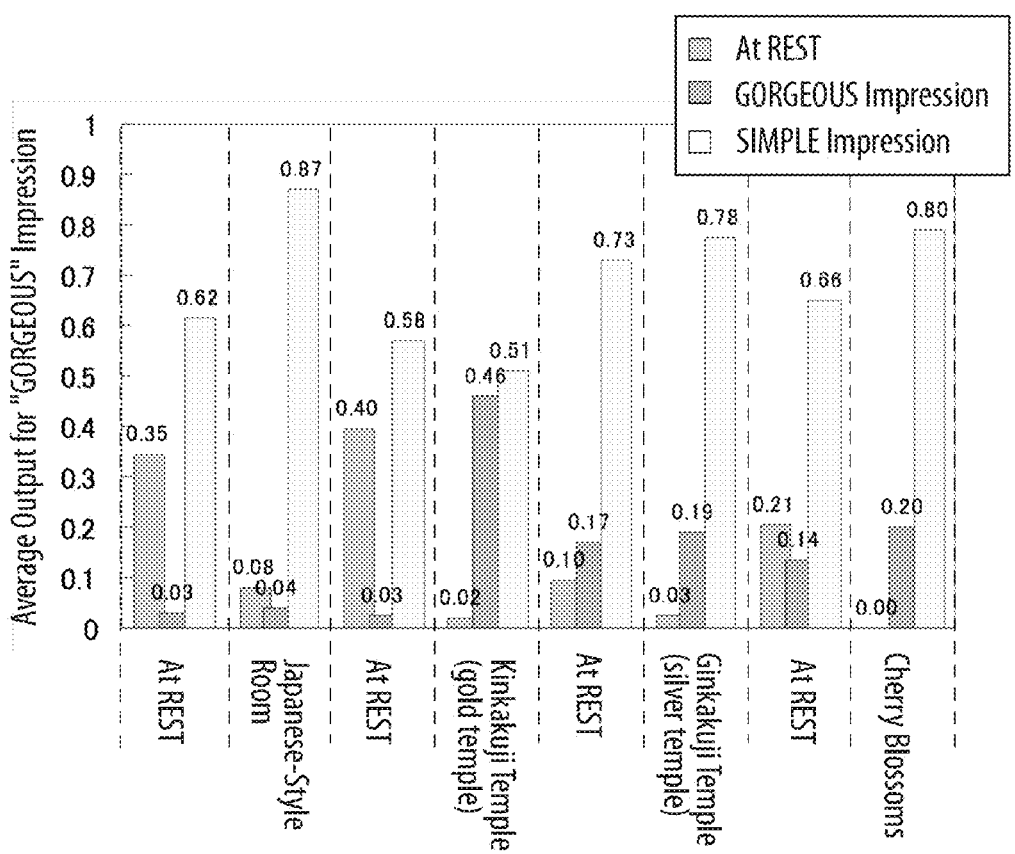
FIG. 6 illustrates an example of the result of computing a difference signal between every two different brain wave signals in a plurality of sets of brain wave signals selected in terms of permutations from brain wave signals for 16 channels obtained through brain wave measurement performing an emotion multifractal dimension analysis on each difference signal, and averaging the resulting values (to obtain average emotion output values).

FIG. 6 illustrates an example of the result of computing a difference signal between every two different brain wave signals in a plurality of sets of brain wave signals selected in terms of permutations from brain wave signals for 16 channels obtained through brain wave measurement performing an emotion multifractal dimension analysis on each difference signal, and averaging the resulting values (to obtain average emotion output values). In this test, five different values 1 to 5 were used as the Hurst exponent characteristic q. In FIG. 6, an emotional state of "having a simple impression" and an emotional state of "having a gorgeous impression" are clearly distinguished from each other. The difference (relative value) between the average value of emotion outputs during the periods under tasks and the average value of emotion outputs during the resting periods corresponds to the substantial emotion output to be evaluated. Thus, although the outputs for "having a simple impression" are high in the example of FIG. 6, the emotion outputs for "having a simple impression" are not so high since evaluation is performed based on the difference (amount of variation). For the correlation coefficient between the emotion output value and the subjective evaluation, as a matter of course, only the total bias of the emotion output values for "having a simple impression" is varied.

Figure 7:
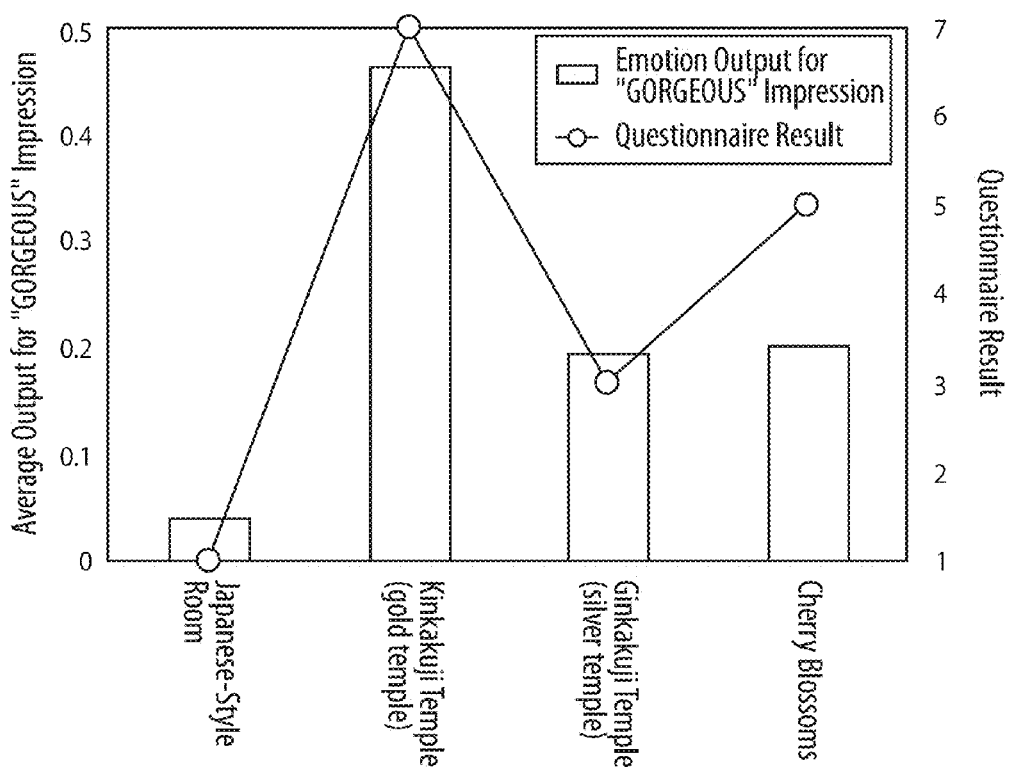
FIG. 7 illustrates the emotion output values for "gorgeous" impression obtained through the task of looking at images extracted from the result of FIG. 6 with the result of questionnaire survey superimposed.
Figure 8:
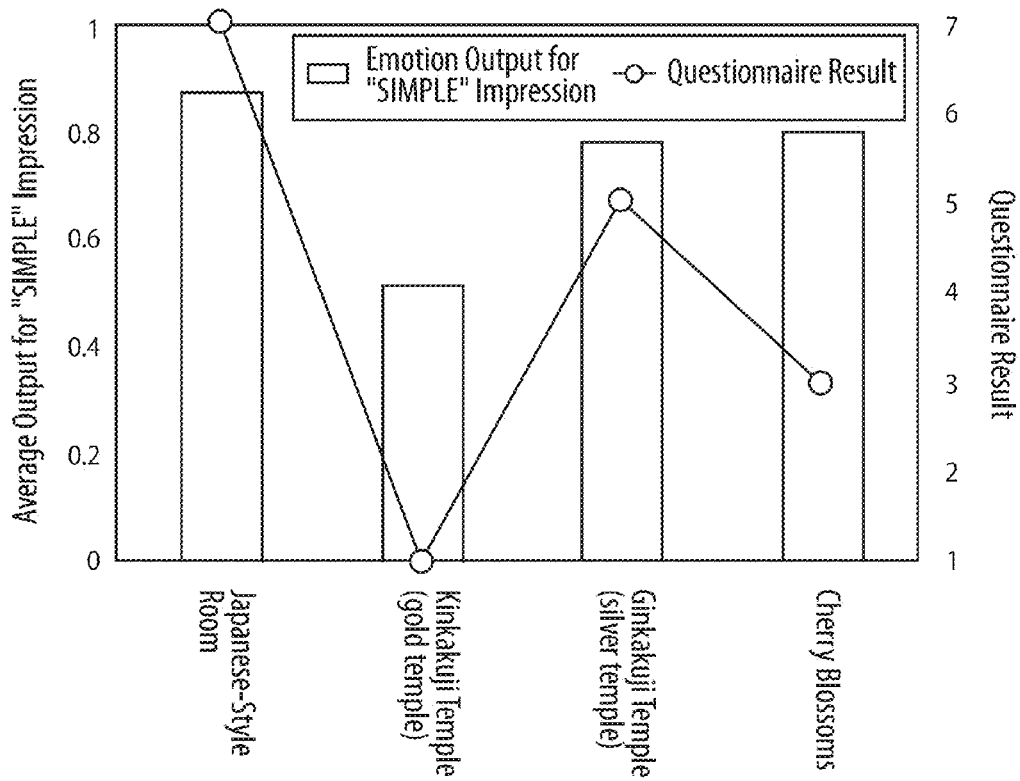
FIG. 8 illustrates the emotion output values for "simple" impression obtained through the task of looking at images extracted from the result of FIG. 6 with the result of questionnaire survey superimposed.

FIGS. 7 and 8 illustrate a questionnaire survey result superimposed on the emotion output values for "having a gorgeous impression" and "having a simple impression", respectively, obtained through the tasks of looking at images extracted from the result of FIG. 6. The correlation coefficient between the emotion output value and the subjective evaluation was 0.94 for "having a gorgeous impression" and 0.88 for "having a simple impression". This shows significantly high determination accuracy.

It has been found that the above results vary among subjects. FIG. 9 shows the correlation coefficient between the emotion output value and the subjective evaluation for each of "having a gorgeous impression" and "having a simple impression" for four subjects. The figures on the left side are values obtained when the conventional technique (related art) disclosed in Japanese Patent Application Publication No. 2004-194924 was adopted. The figures on the right side are values obtained when the technique according to the embodiment of the present invention was adopted. The embodiment of the present invention showed a larger correlation coefficient for any of the four subjects.

In the above embodiment, signals for 16 channels are used. When only one brain wave difference signal is used, however, an emotional state can be effectively distinguished using as the multifractal dimensions generalized latent dimensions $Dq_1$ to $Dq_n$ obtained by substituting a plurality of different values ($q_1$ to $q_n$) determined in advance for a Hurst exponent characteristic q in a generalized latent dimension $Dq=1/Hq$ which is a reciprocal number of a generalized Hurst exponent Hq obtained from the brain wave difference signal, where $q_1$ to $q_n$ are each a positive number and n is a positive integer. That is, the present invention is also effective when a single electrode is used.

Figure 10:
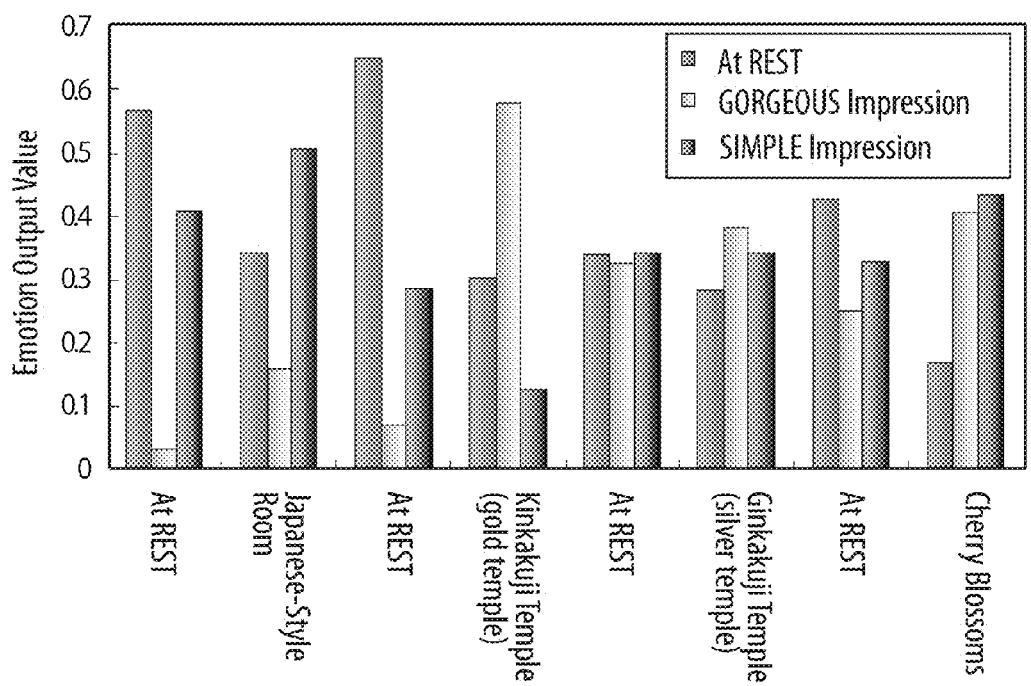
FIG. 10 illustrates an example result (average emotion output values) of performing an emotion multifractal dimension analysis on a brain wave signal for one channel obtained through brain wave measurement.
Figure 11:
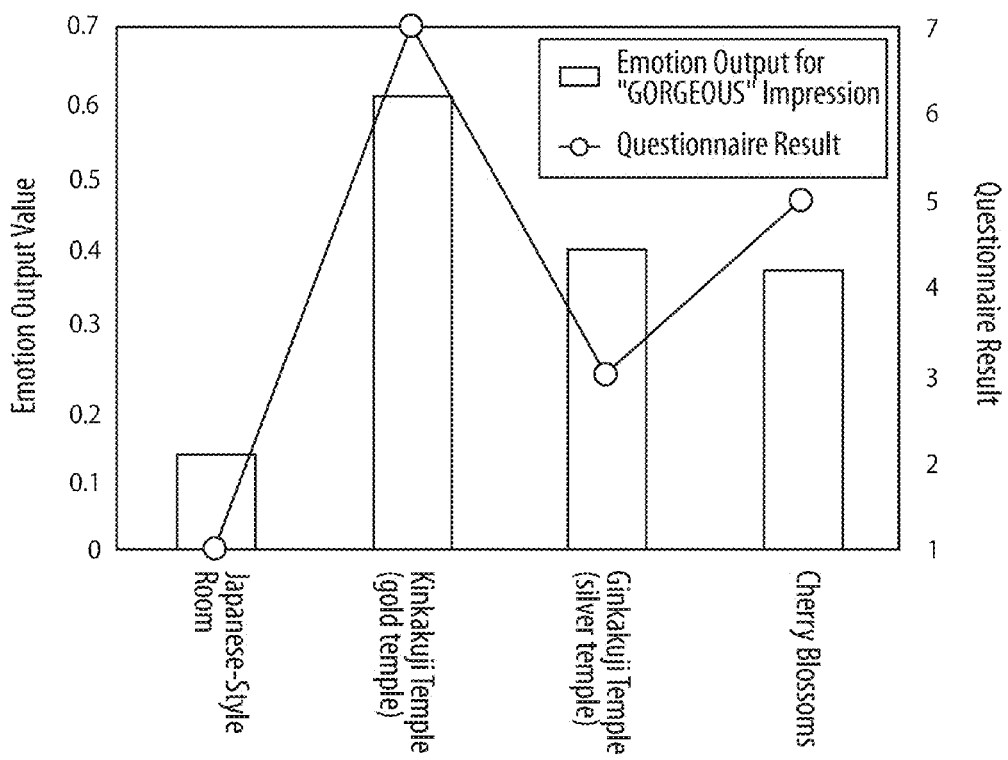
FIG. 11 illustrates the emotion output values for "gorgeous" impression obtained through the task of looking at the images extracted from the result of FIG. 10 with the result of questionnaire survey superimposed.
Figure 12:
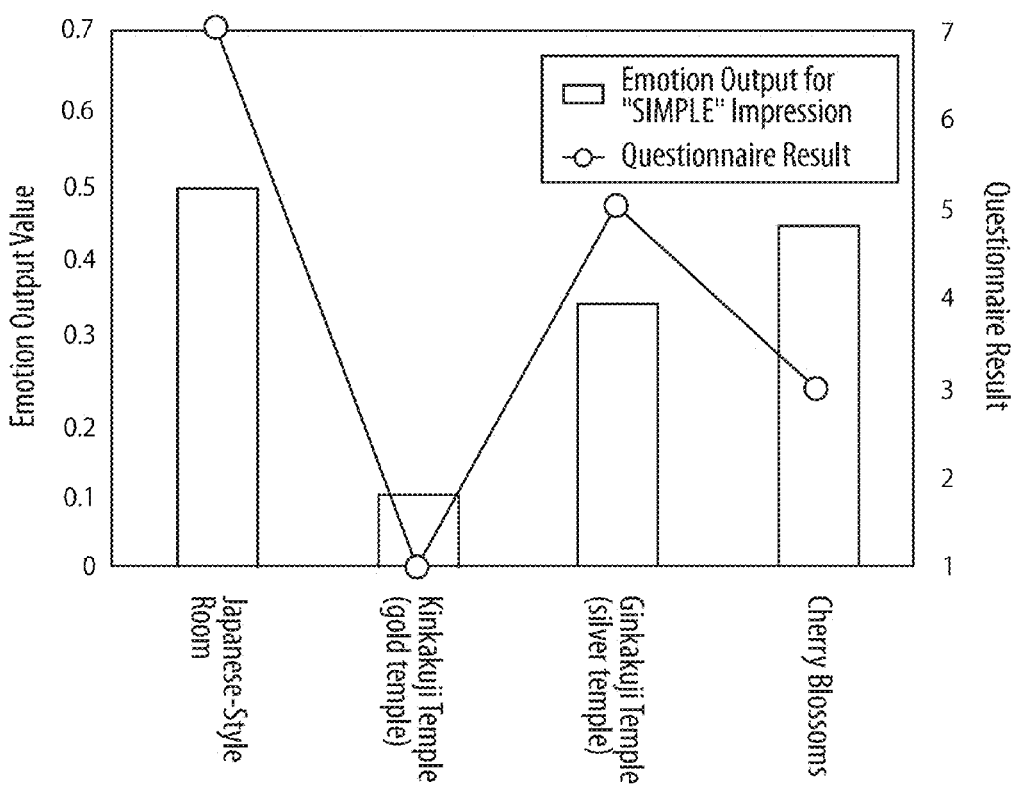
FIG. 12 illustrates the emotion output values for "simple" impression obtained through the task of looking at images extracted from the result of FIG. 10 with the result of questionnaire survey superimposed.

Thus, the same experiment as described above was performed using only a brain wave difference signal between signals from two electrodes attached to the front side of the head portion (a difference in output between channel 1 and the ground electrode in FIG. 2). FIG. 10, which is similar to FIG. 6, illustrates the result of emotion analysis performed on data to be evaluated. FIGS. 11 and 12, which are respectively similar to FIGS. 7 and 8, illustrate a questionnaire survey result superimposed on the emotion output values for "having a gorgeous impression" and "having a simple impression", respectively, obtained through the tasks of looking at images extracted from the result of FIG. 10. The correlation coefficient between the emotion output value and the subjective evaluation was 0.96 for "having a gorgeous impression" and 0.81 for "having a simple impression". This shows that an emotional state can be sufficiently identified even with a single electrode, provided that the electrode makes an output allowing sensitive detection of an emotional state. As a result, according to the present invention in which the generalized latent dimensions are used as the multifractal dimensions, it is possible to effectively perform an emotion analysis by increasing the number of values of the Hurst exponent characteristic q, without reducing the accuracy even if the number of brain wave signals to be used is small (one brain waveform is used).

[Determination Utilizing Neural Net]

Figure 13:
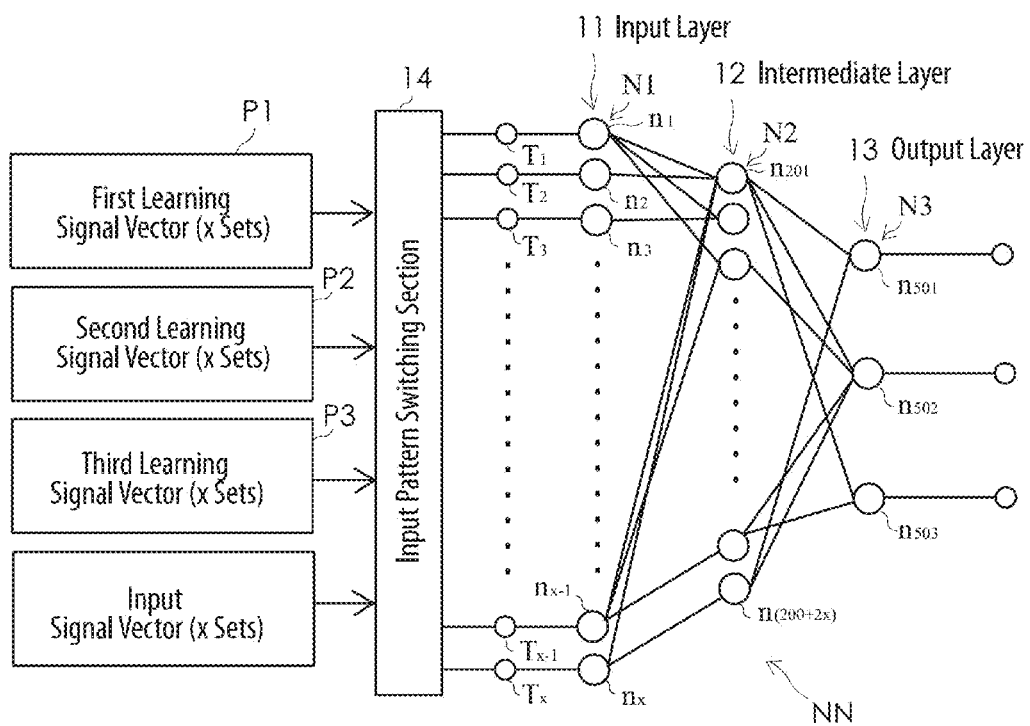
FIG. 13 illustrates an example configuration of an emotional state determining apparatus according to another embodiment of the present invention that utilizes a neural net.

Next, an emotional state determining apparatus according to another embodiment of the present invention will be described below. In this embodiment, an emotion analysis is performed as with the emotional state determining apparatus according to the embodiment of FIG. 1. This embodiment utilizes a neural net as the determination criteria. FIG. 13 illustrates a configuration of the embodiment. In the embodiment, learning for determining the internal state of the neural net is performed in advance to construct the neural net. A neural net NN shown in FIG. 13 includes an input layer 11, one or more intermediate layers 12, and an output layer 13. In this case, one intermediate layer 12 is provided. The input layer 11 includes a first group of neurons N1 formed by x neurons $n_1$ to $n_x$ that respectively receive x multifractal dimensions, where x denotes the number of the combinations of the brain wave difference signals discussed above, that is, $n \times {}_{16}C_2 = 120 \times 5 = 600$. The intermediate layer 12 includes a second group of neurons N2 formed by y ($2 \times x = 1200$) neurons $n_{201}$ to $n_{200+2x}$. The output layer 13 includes a third group of neurons N3 formed by three neurons $n_{501}$ to $n_{503}$. The x (600) neurons $n_1$ to $n_x$ forming the first group of neurons N1 receive three types of learning input patterns, which will be discussed later, and an input signal vector via terminals $T_1$ to $T_x$ of an input pattern switching section 14.

First, in order to determine the internal state of the neural net NN through learning, a plurality of brain wave difference signals are computed in each short time period from a plurality of brain wave signals obtained from the reference person discussed above in a plurality of types of emotional states, and multifractal dimensions are computed in each short time period based on the plurality of brain wave difference signals. Then, the multifractal dimensions for three types of emotional states (being at rest, having a gorgeous impression, and having a simple impression) are determined as three types of learning input patterns. The first learning input pattern includes x sets of multifractal dimensions. That is, a first learning input pattern P1 includes x multifractal dimensions (first learning input signal vector) computed based on the brain wave signals of the reference person in the state of being at rest; a second learning input pattern P2 includes x multifractal dimensions (second learning input signal vector) computed based on the brain wave signals of the reference person having a gorgeous impression; and a third learning input pattern P3 includes x multifractal dimensions (third learning input signal vector) computed based on the brain wave signals of the reference person having a simple impression. The input pattern switching section 14 selects one learning input pattern regularly at predetermined time intervals (0.25 seconds) or irregularly from the three types of learning input patterns obtained from the reference person, and sequentially inputs x sets of data in the selected learning input pattern to the x neurons $n_1$ to $n_x$ forming the first group of neurons N1. The neurons $n_1$ to $n_x$ are each equipped with three types of memories corresponding to the three types of learning input patterns P1 to P3. In case of regular selections, x sets of data are acquired from each pattern in the order of pattern P1, pattern P2, and pattern P3 at time intervals (0.25 seconds) and then input to the x neurons $n_1$ to $n_x$. In case of irregular selections, the patterns are selected in an irregular order such as pattern P1, pattern P1, pattern P3, pattern P2, pattern P3, . . . . Comparing regular pattern selections and irregular pattern selections, it was confirmed through testing that learning was completed in a shorter time through irregular selections than regular selections of patterns.

During learning, the internal state of the neurons $n_1$ to $n_x$, $n_{201}$ to $n_{200+2x}$, and $n_{501}$ to $n_{503}$ and the coupling state between the neurons N1 to N3 are determined such that an output indicating the state of being at rest is output from the three neurons $n_{501}$ to $n_{503}$ forming the third group of neurons N3 of the output layer 13 when the first learning input pattern P1 is input to the first group of neurons N1 of the input layer 11; an output indicating the emotional state of having a gorgeous impression is output from the three neurons $n_{501}$ to $n_{503}$ forming the third group of neurons N3 of the output layer 13 when the second learning input pattern P2 is input to the first group of neurons N1 of the input layer 11; and an output indicating the emotional state of having a simple impression is output from the three neurons $n_{501}$ to $n_{503}$ forming the third group of neurons N3 of the output layer 13 when the third learning input pattern P3 is input to the first group of neurons N1 of the input layer 11.

In the neural net, a sigmoid function is used, the dynamics of which with respect to a discrete time t can be formulated by the following formula:

$$\sigma_{pi}^{(L)}(t+1) = \sum_{j=1}^{N(L-1)} w_{ij}^{(L,L-1)}(t) s_{pj}^{(L-1)}(t+1) + \theta_i^{(L)}(t) \quad \text{[Expression 17]}$$

In the above formula:

$$\sigma_{pi}^{(L)} \quad \text{[Expression 18]}$$

The above expression indicates the internal state of the i-th neuron in the L-th layer with respect to the input pattern p (corresponding to the three input patterns P1 to P3) assuming that the layers from the input layer 11 to the output layer 13 are formed by groups of neurons in L layers. In this example, the L-th layer corresponds to the output layer 13, the L−1-th layer corresponds to the intermediate layer 13, and the $L_0$ layer corresponds to the input layer 11.

$$w_{ij}^{L,L-1} \quad \text{[Expression 19]}$$

The above expression is the coupling load between the neurons j in the L−1-th layer and the neurons i in the L-th layer. In this case, the formula indicates the coupling load between the neurons $n_1$ to $n_x$ in the input layer 11 and the neurons $n_{201}$ to $n_{200+2x}$ in the intermediate layer 12 and the coupling load between the neurons $n_{201}$ to $n_{200+2x}$ in the intermediate layer 12 and the neurons $n_{501}$ to $n_{503}$ in the output layer 13. N (L−1) represents the total number of the neurons in the L−1-th layer.

$$s_{pj}^{(L-1)} \quad \text{[Expression 20]}$$

The above expression is an output from the L−1-th layer.

$$\theta_i^{(L)} \quad \text{[Expression 21]}$$

The above expression is a threshold.

In this example, the neurons in the input layer 11, the intermediate layer 12, and the output layer 13 are activated using the following activation function:

$$f(\sigma_{pi}^{(L)}(t)) = \tanh\left(\frac{\sigma_{pi}^{(L)}(t)}{\varepsilon}\right) \quad \text{[Expression 22]}$$

In the above formula, $\varepsilon$ is a temperature parameter. The output from the output layer 13 is represented by the following formula:

$$s_{pi}^{(L)}(t) = f(\sigma_{pi}^{(L)}(t)) \quad \text{[Expression 23]}$$

During learning, the internal state of the neurons is determined such that the following evaluation function E(t) becomes as small as possible:

$$E(t) = \frac{1}{2P} \sum_{p=1}^{P} \sum_{i=1}^{N(L_0)} \left(t_{pi} - s_{pi}^{(L_0)}(t)\right)^2 \quad \text{[Expression 24]}$$

In the above formula, P is the number of the patterns, N ($L_0$) is the number of the neurons in the input layer 11, $t_{pi}$ is an instruction signal for the p-th pattern for the i-th neuron in the output layer 13, and $$s_{pi}^{L0)}$$ [Expression 25]

The above expression is the p-th pattern for the i-th neuron in the output layer 13.

When the input pattern switching section 14 inputs the input signal vector (x sets) from the subject to the neurons $n_1$ to $n_x$ in the input layer 11 of the neural net NN at predetermined time intervals after the internal state of the neurons in the neural net NN is determined based on the three types of learning input patterns as described above, the neurons $n_{501}$ to $n_{503}$ in the output layer 13 of the neural net NN output the determination results.

Figure 14:
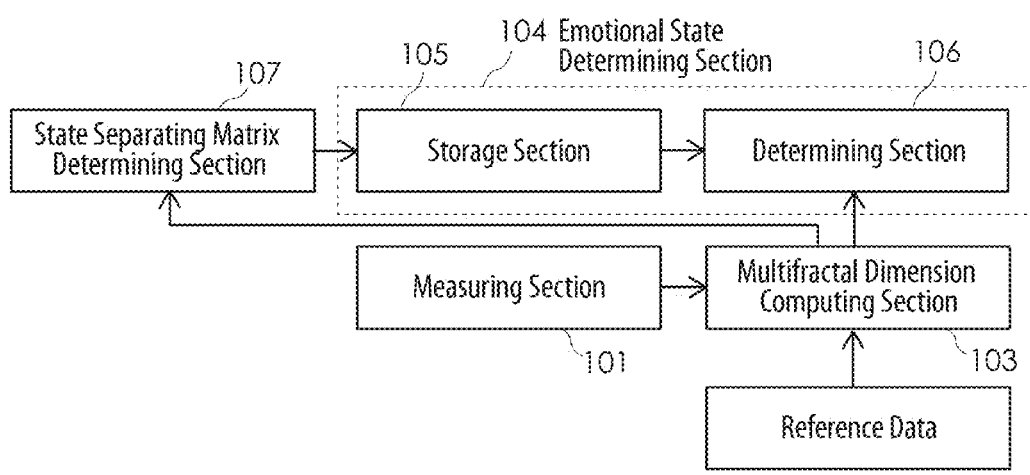
FIG. 14 is a block diagram schematically showing an example configuration of an emotional state determining apparatus according to still another embodiment of the present invention that receives input brain wave signals as they are.

FIG. 14 illustrates a configuration of an emotional state determining apparatus according to still another embodiment of the present invention. In this embodiment, an emotion analysis is performed using one or more brain wave signals measured by a measuring section 101. In FIG. 14, constituent elements that are the same as those in the embodiment shown in FIG. 1 are denoted by reference numerals obtained by adding 100 to the reference numerals affixed to their counterparts in FIG. 1 and detailed descriptions thereof are omitted.

In the embodiment of FIG. 14, unlike the embodiment of FIG. 1, a brain wave difference signal between two brain wave signals is not used. Therefore, the emotional state determining apparatus according to the embodiment of FIG. 14 does not include a constituent element corresponding to the brain wave difference signal computing section 2 of FIG. 1. The measuring section 101 measures one or more brain wave signals with one or more electrodes for measurement disposed at the head portion of the subject. In the simplest case, an emotion analysis is performed using only one brain wave signal output from one electrode. Thus, the present embodiment is the same as the embodiment of FIG. 1 except that a multifractal dimension computing section 103 receives one or more brain wave signals and one or more reference brain wave signals (reference data).

In the embodiment in which the brain wave signals are used as they are, as in the embodiment of FIG. 1, a state matrix determining section 107 is used to determine a state matrix in order to perform a linear analysis using a linear mapping. The state matrix determining section 107 receives the multifractal dimensions as the input signal vector for the determination formula discussed above, and determines the state separating matrix and the constant vector in advance such that, when the reference person is in each of the plurality of types of emotional states, the computation result of the determination formula indicates an emotional state corresponding to each of the plurality of types of emotional states. The multifractal dimension computing section 103 computes the multifractal dimensions based on one or more brain wave signals (reference data) measured from a plurality of regions of the brain of the reference person in each of the plurality of types of emotional states.

Noise may inevitably be influential when brain wave signals are used as they are as in the embodiment, rather than when brain wave difference signals are used. Even when the brain wave signals are directly used, however, information required to perform an emotion analysis can be obtained by increasing the number of values of q in the generalized Hurst exponent Hq described above compared to when the brain wave difference signals are used, thereby causing no practical problem. An experiment performed by the inventor confirmed that the emotion analysis accuracy obtained when brain wave signals were used as they were was lower than the experiment result of FIGS. 10 to 12 wherein one brain wave difference signal was used. However, the experiment also confirmed that no practical problem was caused with the lower emotion analysis accuracy. Also when brain wave signals are used as they are, the analysis accuracy can be enhanced by performing a non-linear analysis using a neural net.

In order to enhance the generality, the determination criteria (state separating matrix, neural net, or the like) are preferably determined using reference data obtained from the reference person who can be intentionally in one of the state of being at rest and the plurality of types of emotional states, rather than from the subject, regardless of whether a non-linear analysis or a linear analysis is used.

INDUSTRIAL APPLICABILITY

By using the generalized latent dimensions as the multifractal dimensions as in the present invention, a desired number of multifractal dimensions can be obtained by increasing the number of values of q in the generalized Hurst exponent Hq. As a result, according to the present invention, it is advantageously possible to effectively perform an emotion analysis by increasing the number of values of q, without significantly reducing the accuracy even if the number of brain wave signals to be used is small (one brain waveform is used).

The invention claimed is:

1. An emotional state determining apparatus comprising:
   a multifractal dimension computing section configured to compute multifractal dimensions based on one or more brain wave signals measured in one or more regions of a subject's brain, or based on one or more brain wave difference signals, each of which is obtained as a difference between two different brain wave signals in one or more sets of the two different brain wave signals that are selected from a plurality of brain wave signals measured in a plurality of regions of the subject's brain; and
   an emotional state determining section configured to receive data on the multifractal dimensions as inputs and determine an emotional state of the subject based on determination criteria which are determined in advance by using as reference data the one or more brain wave signals or the one or more brain wave difference signals obtained from a reference person in each of a plurality of types of emotional states which are determined in advance,
   the emotional state determining section comprising:
      a storage section configured to store the determination criteria; and
      a determining section configured to determine one of the plurality of types of emotional states as the emotional state of the subject based on the determination criteria and the data on the multifractal dimensions, wherein:
   the determination criteria stored in the storage section are defined such that reference multifractal dimensions are computed based on the one or more brain wave signals or the one or more brain wave difference signals obtained as the reference data from the reference person in each of the plurality of types of emotional states and that, when the reference multifractal dimensions for each of the plurality of types of emotional states are input to the determining section, the determining section correctly determines the emotional state corresponding to the input reference multifractal dimensions; and
   the multifractal dimensions are generalized latent dimensions $Dq_1$ to $Dq_n$ respectively obtained by substituting n different values ($q_1$ to $q_n$) determined in advance for a Hurst exponent characteristic q in a generalized latent dimension $Dq=1/Hq$ which is a reciprocal number of a generalized Hurst exponent Hq obtained from the one or more brain wave signals or the one or more brain wave difference signals, where $q_1$ to $q_n$ are each a positive number and n is a positive integer of 2 or more.

2. The emotional state determining apparatus according to claim 1, wherein the determining section is configured to determine m types of emotional states according to a linear mapping determination technique using the following determination formula:

$$\begin{pmatrix} C_{1,1} & C_{1,2} & \cdots & \cdots & C_{1,x} \\ \vdots & \vdots & \ddots & & C_{2,x} \\ \vdots & \vdots & & \ddots & \vdots \\ C_{m,1} & C_{m,2} & \cdots & \cdots & C_{m,x} \end{pmatrix} \begin{pmatrix} y_1 \\ \vdots \\ y_x \end{pmatrix} + \begin{pmatrix} d_1 \\ d_2 \\ \vdots \\ d_m \end{pmatrix} = \begin{pmatrix} z_1 \\ z_2 \\ \vdots \\ z_m \end{pmatrix} \quad \text{[Expression 26]}$$

where:

m is a positive integer of 2 or more;

x is a number represented by x=p×n with the proviso that p is the number of the one or more brain wave signals or the one or more brain wave difference signals; and in the above formula, $$\begin{pmatrix} C_{1,1} & C_{1,2} & \cdots & \cdots & C_{1,x} \\ \vdots & \vdots & \ddots & & C_{2,x} \\ \vdots & \vdots & & \ddots & \vdots \\ C_{m,1} & C_{m,2} & \cdots & \cdots & C_{m,x} \end{pmatrix} \quad \text{[Expression 27]}$$

is a state separating matrix which is a linear mapping;

$$\begin{pmatrix} y_1 \\ \vdots \\ y_x \end{pmatrix} \quad \text{[Expression 28]}$$

is an input signal vector;

$$\begin{pmatrix} d_1 \\ d_2 \\ \vdots \\ d_m \end{pmatrix} \quad \text{[Expression 29]}$$

is a constant vector; and $$\begin{pmatrix} z_1 \\ z_2 \\ \vdots \\ z_m \end{pmatrix} \quad \text{[Expression 30]}$$

is a computation result indicating an emotional state for determining the emotional state thus computed as one of the m types of emotional states.

3. The emotional state determining apparatus according to claim 2, further comprising:

a state matrix determining section configured to receive the multifractal dimensions as the input signal vector for the determination formula and determine the state separating matrix and the constant vector in advance such that, when the reference person is in each of the m types of emotional states, the computation result of the determination formula indicates the emotional state corresponding to each of the m types of emotional states, wherein the brain wave difference signal computing section computes the one or more brain wave difference signals which are obtained as a difference between two different brain wave signals in one or more sets of the two different brain wave signals that are selected from two or more brain wave signals measured in two or more regions of the reference person's brain in each of the plurality of types of emotional states, and the multifractal dimension computing section computes the multifractal dimensions from the one or more brain wave difference signals.

4. The emotional state determining apparatus according to claim 2, further comprising:

a state matrix determining section configured to receive the multifractal dimensions as the input signal vector for the determination formula and to determine the state separating matrix and the constant vector in advance such that, when the reference person is in each of the plurality of types of emotional states, the computation result of the determination formula indicates an emotional state corresponding to each of the plurality of types of emotional states, wherein the multifractal dimension computing section computes the multifractal dimensions from one or more brain wave signals measured in a plurality of regions of the reference person's brain in each of the plurality of types of emotional states.

5. The emotional state determining apparatus according to claim 1, further comprising:

a brain wave difference signal computing section configured to compute difference signals for a plurality of sets of two different brain wave signals, the plurality of sets of two brain wave signals being selected in terms of permutations from the plurality of brain wave signals to output resulting difference signals as the one or more brain wave difference signals.

6. The emotional state determining apparatus according to claim 1, further comprising:

a brain wave difference signal computing section configured to output as the brain wave difference signal a difference signal between two signals from two electrodes disposed at a head portion of the subject corresponding to a frontal lobe portion of the subject's brain.

7. The emotional state determining apparatus according to claim 5, wherein:

the emotional state determining section is configured to determine an emotional state using a neural net as the determination criteria; and an internal state of the neural net is determined by computing the plurality of brain wave difference signals from the plurality of brain wave signals obtained from the reference person in each of the m types of emotional states, computing the multifractal dimensions from the plurality of brain wave difference signals, defining the multifractal dimensions for the m types of emotional states as m types of learning input patterns, and learning using sequentially input data on the learning input patterns selected regularly at predetermined time intervals or irregularly from the m types of learning input patterns.

8. The emotional state determining apparatus according to claim 1, wherein:
the emotional state determining section is configured to determine an emotional state using a neural net as the determination criteria; and
an internal state of the neural net is determined by computing the multifractal dimensions from one of the brain wave signals or one of the brain wave difference signals obtained from the reference person in each of the m types of emotional states, defining the multifractal dimensions for the m types of emotional states as m types of learning input patterns, and learning using sequentially input data on the learning input patterns selected regularly at predetermined time intervals or irregularly from the m types of learning input patterns.

* * * * *